United States Patent [19]
Min

[11] Patent Number: 5,855,752
[45] Date of Patent: Jan. 5, 1999

[54] APPARATUS FOR CLEANING GAS SENSOR

[75] Inventor: Byeong Sung Min, Seoul, Rep. of Korea

[73] Assignee: Samsung Electro-Mechanics Co., Ltd., Kyongki-do, Rep. of Korea

[21] Appl. No.: 589,940

[22] Filed: Jan. 23, 1996

[30] Foreign Application Priority Data

Jan. 26, 1995 [KR] Rep. of Korea .................... 1995-1342

[51] Int. Cl.⁶ .................................................. G01N 27/26
[52] U.S. Cl. ............................ 204/402; 363/89; 363/124
[58] Field of Search ........................... 204/402; 205/775; 363/89, 124

[56] References Cited

U.S. PATENT DOCUMENTS 4,740,878  4/1988  Carter et al. ............................. 363/63
5,247,156  9/1993  Favre ...................................... 219/209

FOREIGN PATENT DOCUMENTS 5-209855  8/1993  Japan .

Primary Examiner—Kathryn L. Gorgos
Assistant Examiner—William Leader
Attorney, Agent, or Firm—Lowe Hauptman Gopstein Gilman & Berner

[57] ABSTRACT

An apparatus for cleaning a gas sensor and a method therefor are disclosed. A high voltage is supplied to a heat generating body of the gas sensor for a certain period of time to generate a large amount of heat within a short period of time so as to remove the moisture or miscellaneous gases absorbed into on the surface of the gas sensor, thereby stabilizing the characteristics of the gas sensor. The apparatus includes: a power supply section for receiving an ac voltage from a commercial ac power source to convert it into a rated voltage and an excessive voltage exceeding the rated voltage; and a switching section for supplying the rated voltage to the gas sensor after supplying the excessive voltage of the power supply section to a heat generating body of a gas sensor for a certain period of time. The method for cleaning a gas sensor includes the steps of: supplying an excessive voltage to the heat generating body of the gas sensor; maintaining the excessive voltage for a certain period of time to remove the gas absorbed into the surface of the gas sensor by means of the high heat of the heat generating body; and supplying a rated voltage to the gas sensor to clean the gas sensor.

2 Claims, 3 Drawing Sheets

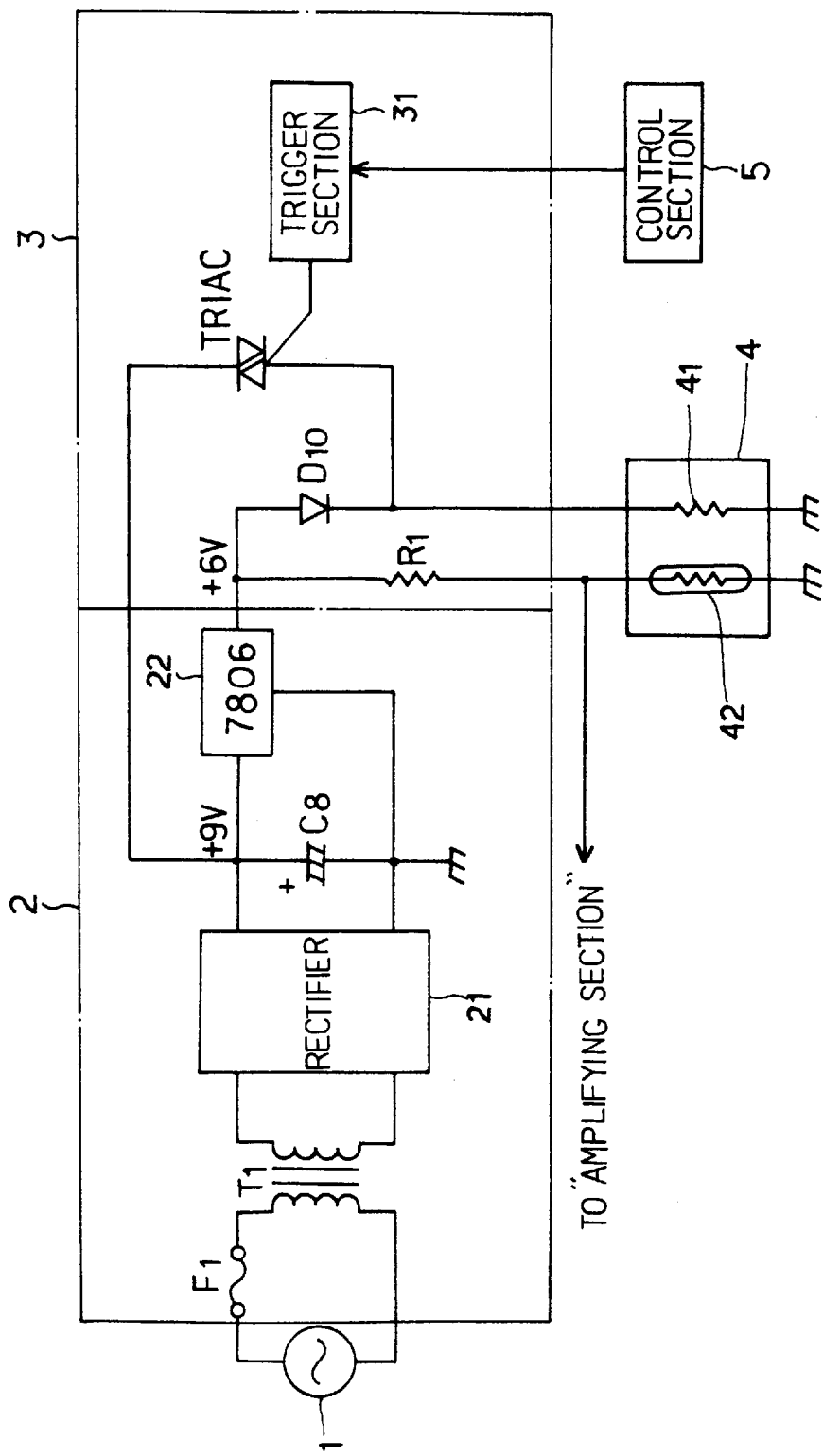

APPARATUS FOR CLEANING GAS SENSOR

FIELD OF THE INVENTION

The present invention relates to an apparatus for cleaning a gas sensor and a method therefor, in which the characteristics of the gas sensor composed of a chemical compound semiconductor are stabilized within a short period of time, thereby improving the product reliability.

BACKGROUND OF THE INVENTION

Generally, a gas sensor senses a gas leakage concentration, and informs of the gas leakage through an external display or an alarm, so that an accident due to a gas leakage can be prevented.

The gas sensor is made by using a metal oxide semiconductor by applying a sintering process. Then the gas sensor is heated on the inside or outside thereof to a certain temperature. Then the sensor element of the gas sensor composed of the metal oxide semiconductor is made to contact an object gas, and then, the varying electric conductivity of the sensor element is measured, thereby recognizing the gas leakage concentration.

The sensing principle of the gas sensor is known to be as follows.

1) Owing to an absorption accompanied by a dissociation of gas and an oxidizing reaction, a migration of electrons occurs between the absorbed molecules and the gas sensor, with the result that the electron density is varied.
2) Owing to a gate action, i.e., a gas absorption, a depleted layer is formed on the surface of the thin film or on the surface of the sintered body.
3) Owing to oxidations and reductions, the chemical composition of the gas sensor is varied.
4) Owing to the self heat generation, the temperature rises, with the result that the electric resistivity is varied.

Due to the material properties, the gas sensor is easily contaminated by the environmental factors such as moisture and miscellaneous gases, and therefore, the gas sensor shows malfunctions in the initial operating days. Therefore, in order to stabilize the characteristics of the gas sensor, the gas sensor is subjected to an aging process after its manufacture by heating it by passing an electric current through it for several hours or several days.

The above described sensor is disclosed in Japanese Patent Application Laid-open No. Hei-5-209855. In this sensor, in order to dissipate a dew formation and to sense a steep humidity variation, a heat generating body is installed on the sensor body to heat the sensor.

Further, in this conventional gas sensor, in order to measure a stabilized resistivity at the manufacturing step, it has to be waited for several days in a state with an electric current flowing, and therefore, the productivity is lowered. Further, a lengthy time period is required before the sensor is restored to the original state after once sensed a gas leakage.

SUMMARY OF THE INVENTION

The present invention is intended to overcome the above described disadvantages of the conventional technique.

Therefore it is an object of the present invention to provide an apparatus for cleaning a gas sensor and a method therefor, in which a high voltage is supplied to a heat generating body of the gas sensor for a certain period of time to generate a large amount of heat within a short period of time so as to remove the moisture or miscellaneous gases absorbed into the surface of the gas sensor, thereby stabilizing the characteristics of the gas sensor.

It is another object of the present invention to provide an apparatus for cleaning a gas sensor and a method therefor, in which moisture or miscellaneous gases are rapidly removed so as to minimize the malfunctions of the gas sensor.

In achieving the above object, the apparatus for cleaning a gas sensor according to the present invention includes: a switching section for supplying a rated voltage to a heat generating body of the gas sensor after supplying an excessive voltage to the heat generating body of the gas sensor.

In another aspect of the present invention, the method for cleaning a gas sensor according to the present invention includes the steps of: supplying an excessive voltage to a heat generating body of the gas sensor; maintaining the excessive voltage for a certain period of time to remove the gas absorbed into the surface of the gas sensor by means of the high heat of the heat generating body; and supplying a rated voltage to the gas sensor to clean the gas sensor.

BRIEF DESCRIPTION OF THE DRAWINGS

The above object and other advantages of the present invention will become more apparent by describing in detail the preferred embodiment of the present invention with reference to the attached drawings in which:

FIG. 3 illustrates another embodiment of the apparatus for cleaning a gas sensor according to the present invention.

DESCRIPTION OF THE PREFERRED EMBODIMENTS

Figure 1:
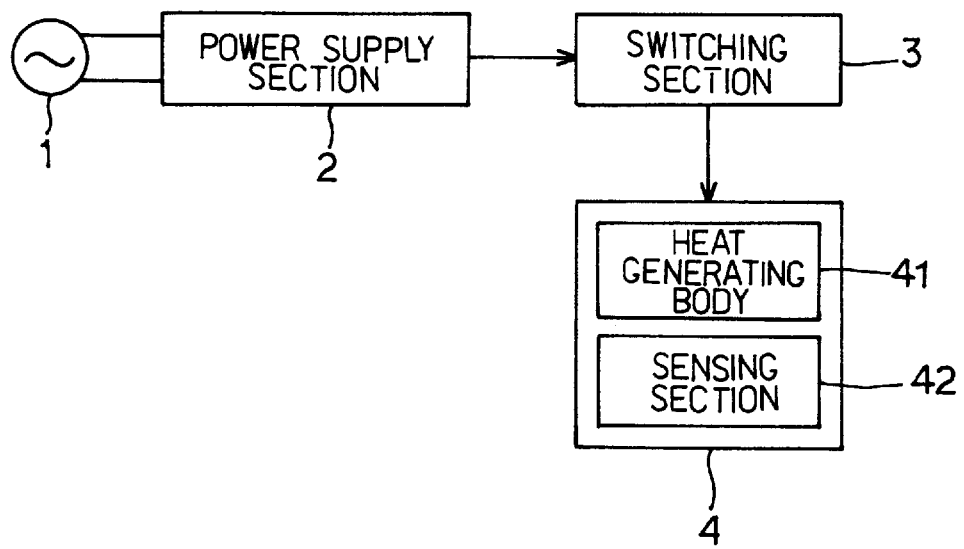
FIG. 1 is a block diagram showing the constitution of the apparatus for cleaning a gas sensor according to the present invention.

FIG. 1 is a block diagram showing the constitution of the apparatus for cleaning a gas sensor according to the present invention.

The apparatus according to the present invention includes: a power supply section 2 for receiving an ac voltage from a commercial ac power source 1 to convert it into a rated voltage and an excessive voltage exceeding the rated voltage; and a switching section 3 for supplying the rated voltage to the gas sensor 4 after supplying the excessive voltage of the power supply section 2 to a heat generating body 41 of a gas sensor 4 for a certain period of time.

Figure 2:
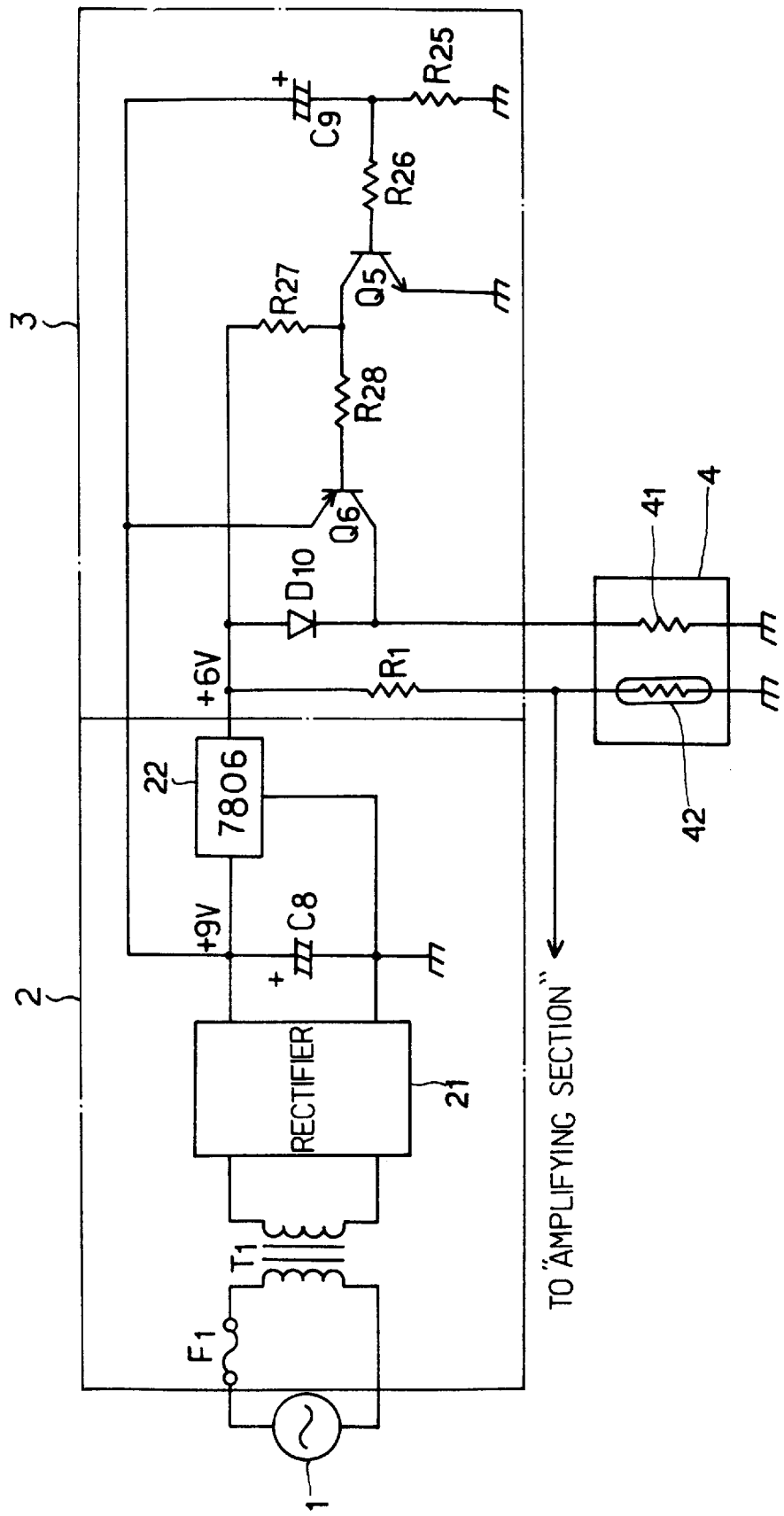
FIG. 2 illustrates the circuit of an embodiment of the apparatus for cleaning a gas sensor according to the present invention.

FIG. 2 illustrates a detailed circuit of an embodiment of the apparatus for cleaning a gas sensor according to the present invention.

The power supply section 2 includes: a transformer T1 for converting an ac voltage to a certain lower voltage; a rectifier 21 for converting the output ac voltage of the transformer T1 to a dc voltage; a smoothing capacitor C8 for removing the ripple component from the rectified voltage of the rectifier 21; and a regulator 22 for converting the output voltage of the smoothing capacitor C8 to a certain voltage.

An ac power of 110V or 220V which is outputted from the commercial ac power source 1 is supplied through a fuse F1 to a primary coil of the transformer T1. Then the voltage of the primary coil is stepped down to a 9V ac power, and then, is outputted to the rectifier 21. The rectifier 21 converts the stepped-down ac voltage to a dc voltage, and in the output of the rectifier 21, there exist ripples. These ripples are removed by the smoothing capacitor C8 so as to be supplied to the heat generating body 41 of the gas sensor 4 as a 9V excessive voltage. The 9V dc voltage is converted into a 6V constant voltage by the regulator 22.

The switching section 3 includes: switching transistors Q5 and Q6; resistors R25, R26, R27 and R28 for biasing the transistors Q5 and Q6; a capacitor C9 for being charged by the 9V excessive dc voltage of the power supply section 2; a bypassing diode D10 connected between the emitter terminal of the switching transistor Q6 and a 6V output terminal of the constant voltage regulator 22; and a resistor R1 connected between a sensing section 42 of the gas sensor 4 and the 6V output terminal of the constant voltage regulator 22, whereby the gas sensor 4 is cleaned within several seconds.

In the switching section 3 constituted as described above, when the power is supplied from the power supply section 2, a certain level of voltage is supplied to the base of a switching transistor Q5 until the capacitor C9 is completely charged, and therefore, the switching transistor Q5 is put to a turned-on state. In this turned-on transistor Q5, it becomes conductive between the collector and the emitter, and therefore, the transistor Q6 in which its base is connected through the resistor R28 to the collector of the transistor Q5 becomes conductive between its emitter and base, with a current flowing therebetween. Then the 9V excessive voltage which is outputted from the power supply section 2 through the turned-on transistor Q6 is supplied to the heat generating body 41 of the gas sensor 4. Thus an excessive amount of heat is generated by the excessive voltage, and the generated heat is transferred to the sensing section 42 of the gas sensor 4. By this heat, there are desorbed and removed the moisture and the miscellaneous gases which have been absorbed into the sensing section 42.

The heat generating body 41 is made of a steel nichrome wire, and its electrical resistance is about 30Ω which however is varied in accordance with the material and type of the gas sensor 4. The heat amount Q which is decided by the value of the resistance is defined as follows.

$$Q=0.24 I^2 R t$$

where I is the current, R is the resistance, and t is the time.

Further, the heating time is decided by taking into account the specific heat and mass of the gas sensor 4. When the heating time is decided, the values of the capacitor C9 and the resistance R25 are decided in such a manner that the heating time should be equal to the time constant which is decided by the values of the capacitor C9 and the resistor R25.

When the excessive voltage is supplied to the heat generating body for a time period corresponding to the time constant, a large amount of heat is generated by the excessive voltage, and the generated heat is transferred to the sensing section 42 of the gas sensor 4. By this heat, the moisture and the miscellaneous gases which have been absorbed into the sensing section 42 are desorbed and removed.

When the time period of the time constant is elapsed away, the capacitor C9 is fully charged, and no voltage is supplied to the base of the transistor Q5, but the transistor Q5 is turned off. Instead, a voltage is supplied through a resistor R27 to the base of the transistor Q6, so that the transistor Q6 would be turned off. Consequently, the 9V dc voltage is not supplied through the transistor Q6 to the heat generating body 41, but the 6V dc voltage is supplied through a diode D10 to the heat generating body 41.

The switching section 3 constituted as described above is only one of examples, and other forms are possible. That is, instead of the capacitor C9, there can be used a timer which is enabled only after a certain time period from the supply of the power. Further, instead of the transistor, an electronic switching element (e.g., SCR, TRIAC, etc.) can be used.

FIG. 3 illustrates another embodiment of the apparatus for cleaning a gas sensor according to the present invention.

In this second embodiment, a TRIAC and a trigger section 31 are added in the switching section 3, and a control section 5 is also added. After supplying the power, the control section 5 controls the trigger section 31, so that a trigger signal would be supplied to the gate of the TRIAC, thereby turning on the TRIAC. The 9V dc voltage of the rectifier 21 as supplied through the turned-on TRIAC to the heat generating body 41 of the gas sensor 4. In a state with the 9V dc voltage supplied to the heat generating body 41 of the gas sensor 4, the control section 5 carries out a counting for a certain period of time based on a software program. During the time when the control section 5 carries out the counting, the heat generating body 41 of the gas sensor 4 releases heat continuously so as to heat the sensing section 42. By this heat, the moisture and the miscellaneous gases which have been absorbed into the sensing section 42 are removed.

In the second embodiment, instead of the control section 5, a timer can be used. Further, instead of the TRIAC, there can be used a thyristor which is an ac switching device. In this case, a 9V ac voltage which is outputted from the secondary coil of the transformer T1 is supplied through the thyristor.

According to the present invention as described above, an excessive voltage is supplied to the heat generating body for a certain period of time to generate a large amount of heat, thereby rapidly removing the moisture or miscellaneous gases of the surface of the gas sensor. Consequently, the aging time is shortened, so that the productivity can be improved. Further, there can be shortened the time for recovering the original state for sensing the gas leakage again after one round of gas sensing.

What is claimed is:

1. An apparatus for cleaning a gas sensor having a sensing section and a heat generating body for generating heat, said apparatus comprising:

a power supply section having an input connector, a first output connector for supplying a rated voltage and a second output connector for supplying a voltage in excess of the rated voltage, said power supply section receiving an ac voltage from a power source and converting the ac voltage to the rated voltage and the excess voltage;

and a switching section for supplying the excess voltage to the heat generating body of the gas sensor for a period of time beginning when the excess voltage is initially supplied to the heat generating body of the gas sensor, and supplying the rated voltage to the heat generating body of the gas sensor after the period of time has expired, wherein said switching section comprises:

a capacitor in series with a resistor both connected between the output connector of the power supply section which supplies the excess voltage and ground;

a first electronic switch connected to the junction between the capacitor and resistor for being turned on by receiving a switching voltage from said capacitor for a time period corresponding to a time constant, said time constant being determined by said capacitor and said resistor;

a second electronic switch connected to an output of the first electronic switch for being turned on by said first electronic switch and having an excess voltage output terminal to supply the excess voltage to the heat generating body of the gas sensor; and a bypassing diode bypassing the first and second electronic switches and having a cathode connected to the excess voltage output terminal of said second electronic switch, and an anode connected to the output connector of the power supply section for supplying the rated voltage.

2. An apparatus for cleaning a gas sensor having a sensing section and a heat generating body for generating heat, said apparatus comprising:

a power supply section having an input connector, a first output connector for supplying a rated voltage and a second output connector for supplying a voltage in excess of the rated voltage, said power supply section receiving an ac voltage from a power source and converting the ac voltage to the rated voltage and the excess voltage, and a switching section for supplying the excess voltage to the heat generating body of the gas sensor for a period of time beginning when the excess voltage is initially supplied to the heat generating body of the gas sensor, and supplying the rated voltage to the heat generating body of the gas sensor after the period of time has expired, wherein said switching section comprises:

an electronic switch for supplying the excess voltage to the heat generating body of the gas sensor;

a trigger section for triggering said electronic switch;

a control section for activating said trigger section to turn on said electronic switch for said period of time;

and a bypassing diode bypassing the electronic switch and having a cathode connected to an excess voltage output terminal of said electronic switch, and an anode connected to the output connector of the power supply section supplying the rated voltage.

* * * * *